(12) United States Patent
Imran et al.

(10) Patent No.: US 9,643,005 B2
(45) Date of Patent: May 9, 2017

(54) SWALLOWABLE CAPSULE AND METHOD FOR STIMULATING INCRETIN PRODUCTION WITHIN THE INTESTINAL TRACT

(71) Applicant: InCube Labs, LLC, San Jose, CA (US)

(72) Inventors: Mir Imran, Los Altos Hills, CA (US); Mir Hashim, Fremont, CA (US); Emily Arnsdorf, Mercer Island, WA (US)

(73) Assignee: Incube Labs, LLC, San Jose, CA (US)

( * ) Notice: Subject to any disclaimer, the term of this patent is extended or adjusted under 35 U.S.C. 154(b) by 0 days.

(21) Appl. No.: 15/192,928

(22) Filed: Jun. 24, 2016

(65) Prior Publication Data

US 2017/0028195 A1  Feb. 2, 2017

Related U.S. Application Data

(60) Continuation of application No. 14/599,350, filed on Jan. 16, 2015, now Pat. No. 9,403,002, which is a continuation of application No. 14/273,917, filed on May 9, 2014, now Pat. No. 8,958,879, which is a continuation of application No. 14/179,215, filed on Feb. 12, 2014, now Pat. No. 8,781,591, which is a division of application No. 12/849,574, filed on Aug. 3, 2010, now Pat. No. 8,682,440.

(60) Provisional application No. 61/273,389, filed on Aug. 3, 2009.

(51) Int. Cl.
*A61N 1/05* (2006.01)
*A61N 1/36* (2006.01)

(52) U.S. Cl.
CPC ....... *A61N 1/36007* (2013.01); *A61N 1/0509* (2013.01)

(58) Field of Classification Search
CPC .. A61N 1/36007; A61N 1/0509; A61B 5/103; A61B 5/681; A61B 2567/162
See application file for complete search history.

(56) References Cited

U.S. PATENT DOCUMENTS

| 2007/0016262 | A1* | 1/2007 | Gross | A61N 1/36007 607/40 |
| 2009/0030473 | A1* | 1/2009 | Khawaled | A61N 1/36007 607/40 |

* cited by examiner

*Primary Examiner* — Paula J Stice
(74) *Attorney, Agent, or Firm* — Wilson Sonsini Goodrich & Rosati; Joel M. Harris (57) ABSTRACT

Embodiments of the invention provide apparatus and methods for stimulating L cells in the intestinal tract to produce incretins for the treatment of conditions including diabetes and obesity. Many embodiments provide a method and apparatus for the treatment of diabetes by electrically stimulating L-cells to secrete incretins to stimulate or otherwise modulate the production of insulin. Particular embodiments provide a swallowable capsule for stimulating L-cells in the intestinal tract as the capsule moves through the tract. The capsule can include two or more electrodes for providing electrical stimulation to L-cells, a power source for powering one or more components of the capsule, a sensor for sensing the location of the capsule in the intestinal tract; a controller and a waveform generator for generating the electrical signals emitted by the electrodes to stimulate the L-cells to secrete incretins such as GLP-1 to stimulate insulin production for glucose regulation of diabetic conditions.

29 Claims, 11 Drawing Sheets

SWALLOWABLE CAPSULE AND METHOD FOR STIMULATING INCRETIN PRODUCTION WITHIN THE INTESTINAL TRACT

CROSS-REFERENCES TO RELATED APPLICATIONS

The present application is a continuation of U.S. Pat. No. 9,403,002, filed Jan. 16, 2015, which is a continuation of U.S. Pat. No. 8,958,978, filed May 9, 2014, which is a continuation of U.S. Pat. No. 8,781,591, filed Feb. 12, 2014, which is a divisional of U.S. Pat. No. 8,882,440, filed Aug. 3, 2010; which claims the benefit of Provisional Application No. 61/273,389, filed Aug. 3, 2009; the entire contents of which are incorporated herein by reference.

BACKGROUND OF THE INVENTION

Field of the Invention

Embodiments described herein relate to apparatus and methods for electrically stimulating cells in the GI system to produce polypeptides for the treatment of various conditions such as diabetes and obesity. More specifically, embodiments of the invention relate to treatment of diabetes by electrically stimulating cells in the gastrointestinal (GI) system to produce glucose regulating hormones such as incretins.

Due to the increasing consumption of high fat and/or high caloric foods found in the western diet, there has been an epidemic in the United States and other developed countries of diabetes and obesity. Diabetes is a disease in which the body does not produce enough, or properly respond to, insulin, a hormone produced in the pancreas. Insulin is needed to turn sugar and other food into energy. In diabetes, the body either doesn't make enough insulin or can't use its own insulin as well as it should, or both. This causes sugar to accumulate in the blood, often leading to various complications. The American Diabetes Association reported in 2009 that there are 23.6 million children and adults in the United States (equal to about 7.8% of the total population) who have diabetes. While an estimated 17.9 million in the US alone have been diagnosed with diabetes, nearly one in four (5.7 million) diabetics are unaware that they have the disease.

The main types of diabetes include type 1, type 2 and gestational diabetes. Type 1 diabetes results from the body's failure to produce insulin. It is estimated that 5-10% of Americans who are diagnosed with diabetes have type 1 diabetes. Presently almost all persons with type 1 diabetes must take insulin injections.

Type 2 diabetes results from a condition in which the body fails to use insulin properly, combined with a relative insulin deficiency. Most Americans who are diagnosed with diabetes have type 2 diabetes. Many people destined to develop type 2 diabetes spend many years in a state of pre-diabetes: Termed "America's largest healthcare epidemic, a condition that occurs when a person's blood glucose levels are higher than normal but not high enough for a diagnosis of type 2 diabetes. As of 2009 there were 57 million Americans who have pre-diabetes. In the developed world, diabetes is the most significant cause of adult blindness in the non-elderly and the leading cause of non-traumatic amputation in adults. Furthermore, diabetic nephropathy is the main illness requiring renal dialysis in the United States.

Most forms of diabetes have been treatable, in part, since insulin became medically available in the 1920's. Currently, many diabetics monitor their blood glucose using blood glucose meters and give themselves insulin injections one or more times a day. However, this approach has many complications due to the under or over delivery of insulin as well as a long-term inability to regulate blood glucose. Acute complications including hypoglycemia, diabetic ketoacidosis, or non-ketotic hyperosmolar coma may occur if the disease is not adequately controlled. Serious long-term complications include cardiovascular disease, chronic renal failure, retinal damage (which may lead to blindness), nerve damage, and micro-vascular damage (which may cause erectile dysfunction and poor wound healing). Poor healing of wounds, particularly of the feet, can lead to gangrene, and possibly to amputation.

Other forms of drug therapy are also available, such as Metformin (known as GLUCOPHAGE). However, this drug is only indicated for the treatment of type II non-insulin dependent diabetes and has a number of side effects including various gastrointestinal side effects. Also, it may not be used with patients who have renal disease. Other forms of treatment include implantabable insulin pumps; however, these are costly and ultimately become rejected by the body. Thus there is a need for improved forms of treatment of diabetes and other glucose regulation disorders.

Obesity, defined as a body mass index (BMI) of greater than 30, is a major health concern in the United States and other countries. It has been estimated that one in three Americans and more than 300 million people world-wide are obese. Complications of obesity include many serious and life-threatening diseases including hypertension, diabetes, coronary artery disease, stroke, congestive heart failure, pulmonary insufficiency, multiple orthopedic problems, various cancers and a markedly decreased life expectancy. Many therapies have been attempted for the treatment of obesity including diets, drugs and more invasive treatments such as stomach stapling. However, many fail due to the inability to invoke the satiety signal pathways which indicate to a person when they are full. Research now indicates that many foods being supplied by the foods industry, including those high in salt, sugar and fat, invoke a strong signal response in the brain to keep eating. Thus there is a need for improved forms of obesity treatment including those which can stimulate satiety signals and/or appetite suppression signals to cause the person to stop eating or otherwise suppress their appetite.

BRIEF SUMMARY OF THE INVENTION

Embodiments of the invention provide apparatus and methods for stimulating L-cells of the small intestine to produce incretins and other peptides for the treatment of various diseases and conditions including diabetes and obesity. Many embodiments provide a method and apparatus for the treatment of obesity, diabetes and other glucose regulation disorders by electrically stimulating L-cells to secrete glucagon-like proteins (GLP, also referred to herein as glucagon-like peptides) and other incretins to stimulate the production of insulin. Particular embodiments provide a swallowable capsule for electrically stimulating L-cells in the intestinal tract to secrete GLPs as the capsule moves through the intestinal tract. Embodiments of the capsule can include two or more electrodes for providing electrical stimulation to L-cells, a sensor for sensing the location of the capsule in the intestinal tract, a power source such as a battery for powering one more electrical components within the capsule, and a controller for controlling one or more operations of the capsule and a signal/waveform generator for generating the electrical signals delivered to the tissue by the electrodes to stimulate the L-cells to produce incretins such as glucagon-like peptide-1 (GLP-1). The signals will typically comprise a waveform such as a square-wave having a selectable pulse duration and may be generated by a signal/waveform generator integral to or coupled to the controller. Desirably, the signal is configured such that it will stimulate the L-cells to secrete incretins, such as GLP-1, but will not cause peristaltic contractions of the intestinal site near the capsule or any other location in the intestinal tract. However, in some embodiments, the waveform generator can also be configured to produce two waveforms, one waveform for stimulating the L-cells without causing peristaltic contractions and a second waveform for causing peristaltic contractions so as to advance the capsule along the intestinal tract. In these later embodiments, the capsule can include an accelerometer for detecting when the capsule has stopped moving or is moving below a desired velocity threshold. In use, these latter embodiments allow for the capsule to be advanced in patients who have a very slow moving intestinal tract such as those patients who have intestinal neuropathy or other related condition such as intestinal necrosis. When the controller receives an input from the accelerometer indicating that the capsule has stopped or is moving too slowly, the controller can send a signal for the waveform generator to generate the second waveform causing peristaltic contraction of the intestine in the region near the capsule which in turn propels the capsule distally through the intestine. The process can be repeated as needed with selectable delays to allow for the refractory period of the peristaltic contraction.

The electrodes will typically include at least one pair of electrodes which can be positioned in a variety of locations and orientations on the surface of the capsule. This can include in a lengthwise fashion with respect to the longitudinal axis or radial axis of capsule. In particular embodiments, the electrodes can comprise one or more pairs of ring electrodes which are placed on the surface capsule. The electrodes can comprise various conductive metals known in the art including silver-silver chloride or platinum, for example. The spacing of the electrodes may be configured to minimize electrical stimulation of tissue subjacent the mucosal layer of intestinal tract. In particular embodiments, the spacing can be configured to limit the electrical stimulation of the intestinal wall to a depth of 5 mm or less.

In various embodiments, the at least one sensor can include one or more of a pH sensor for detecting the passage of the capsule from the stomach into the small intestine and a pressure sensor for sensing the peristaltic contraction of the intestines so as to detect when the capsule is in the intestine (independent of or in combination with an input from the pH sensor). The pressure sensor can also be used to detect when the intestine is in contact with capsule (e.g., when it's being squeezed during a peristaltic contraction) and thus when to initiate a period of stimulation. Particular embodiments can include both pH and pressure sensors so as to determine a change in pH from stomach to intestine as well as a peristaltic contraction providing an increased level of accuracy in determining the position of the sensor within the tract. Still other sensors are contemplated, such as temperature, $O_2$, $CO_2$, optical sensors, etc. The inputs from multiple sensors may also be combined to come up with an aggregate sensory input for the controller to determine the position of the capsule. In various embodiments, sensor conditioning circuitry (e.g., band pass filters) can be coupled to the controller to condition the sensor signals prior to being inputted to the controller.

In an exemplary embodiment of a method of use, the swallowable capsule of the present invention can be used to stimulate L-cell secretion of various proteins such as GLPs so as to facilitate insulin release and/or enhance its activity in the body. In these and other related embodiments, the user may swallow the capsule before, during or after a meal. Upon ingestion, the swallowable capsule makes its way through the stomach and into the small intestine. Sensors in the capsule allow its relative location in the body to be detected. For example, sensors for pH, pressure, or other pertinent indicia allow the capsule to determine when it has reached the small intestine. Once in the small intestine, the swallowable capsule is activated by a controller (typically within the capsule) to provide electrical stimulation so that L cells of the small intestine secrete GLP-1 or other incretins (GIP, PYY, etc.). The GLP-1 and/or other incretins then elicit secretion of insulin and/or facilitate the body's use of insulin. Activation of the swallowable capsule to provide electrical stimulation may, for example, be directed by internal instructions and/or programs in the swallowable capsule, or may be provided by external control of the swallowable capsule. Preferably, the swallowable capsule is ingested shortly before or with a meal so that the stimulation of secretion of GLP-1 and/or other incretins is coordinated with the absorption of nutrients from the digesting food so that subsequent insulin production is also coordinated with the influx of glucose, fats and other nutrients into the blood stream. In this way, the patient's blood glucose levels can be controlled to more closely approximate those of a normal non-diabetic individual following a meal.

Further details of these and other embodiments and aspects of the invention are described more fully below with reference to the accompanying figures.

BRIEF DESCRIPTION OF THE DRAWINGS

FIGS. 7a-7d are views showing different embodiments for configurations of electrodes on the capsule.

DETAILED DESCRIPTION OF THE INVENTION

Embodiments described herein provide methods and apparatus for stimulating cells in the small intestine to secrete glucagon-like proteins (also referred to herein as glucagon-like peptide) and other hormones and secreted compounds for the treatment of various conditions including diabetes and obesity.

Figure 1:
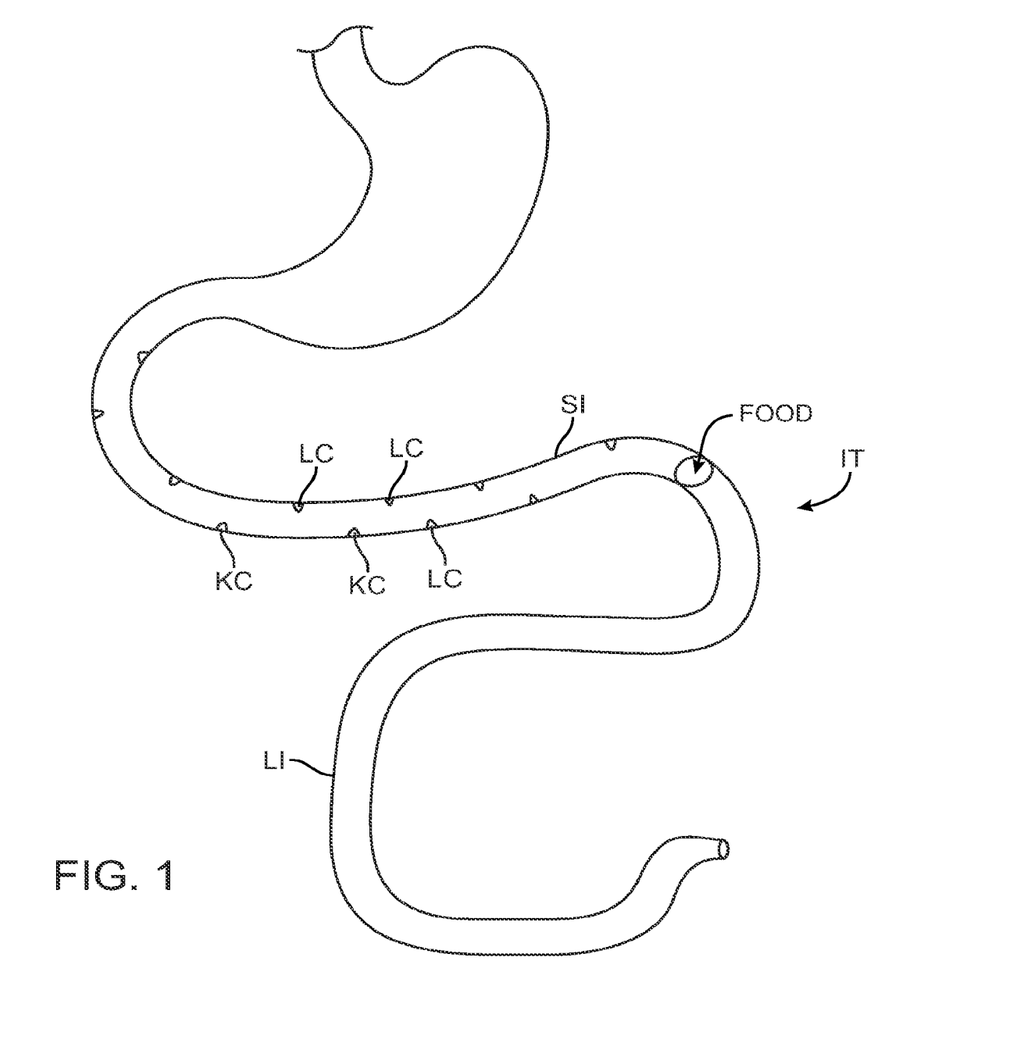
FIG. 1 is a view showing the small intestine and the distribution of L-cells along the intestinal wall.
Figure 2:
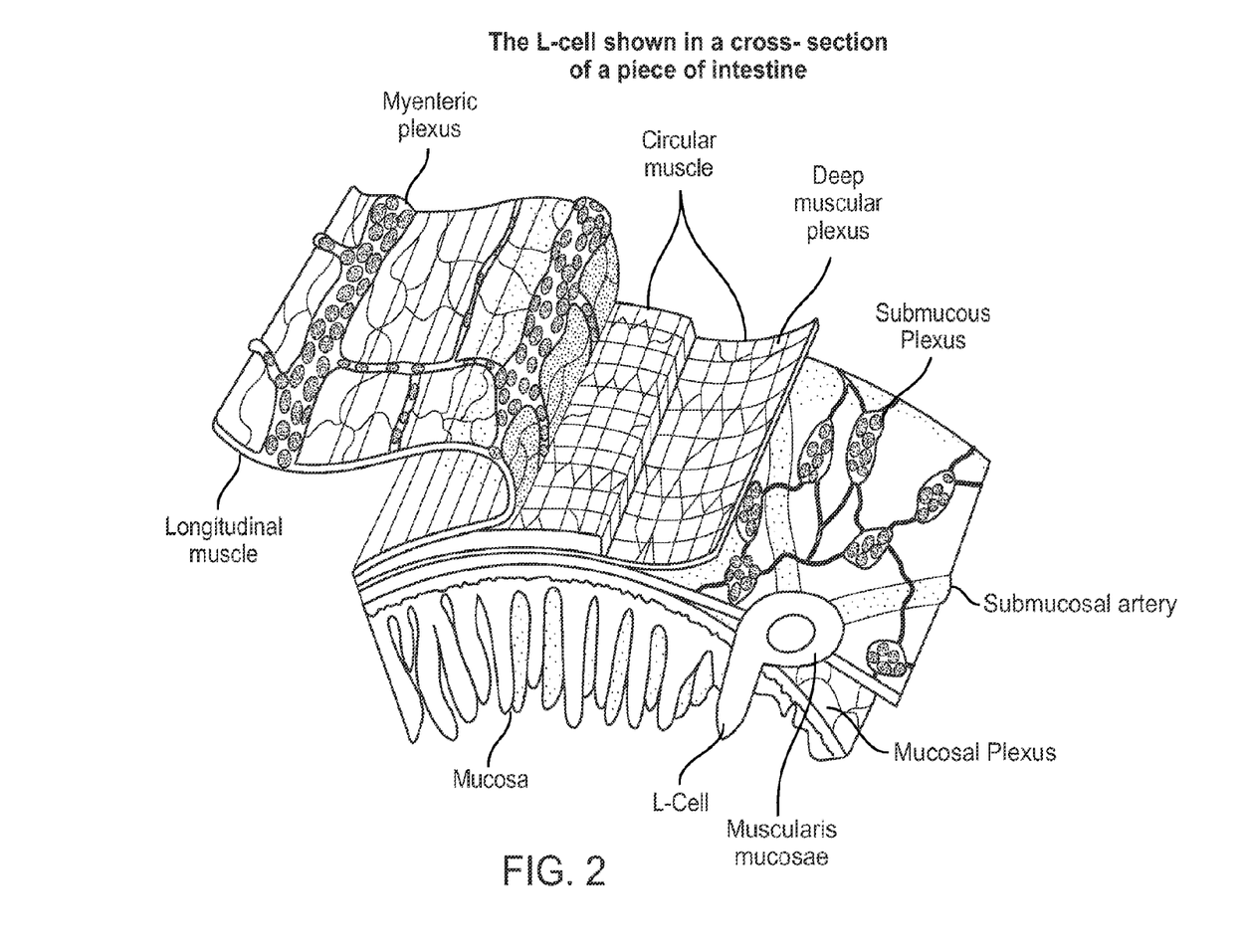
FIG. 2 is a cross sectional view of the intestine showing the position of the L-cell in the intestinal wall.
Figure 3:
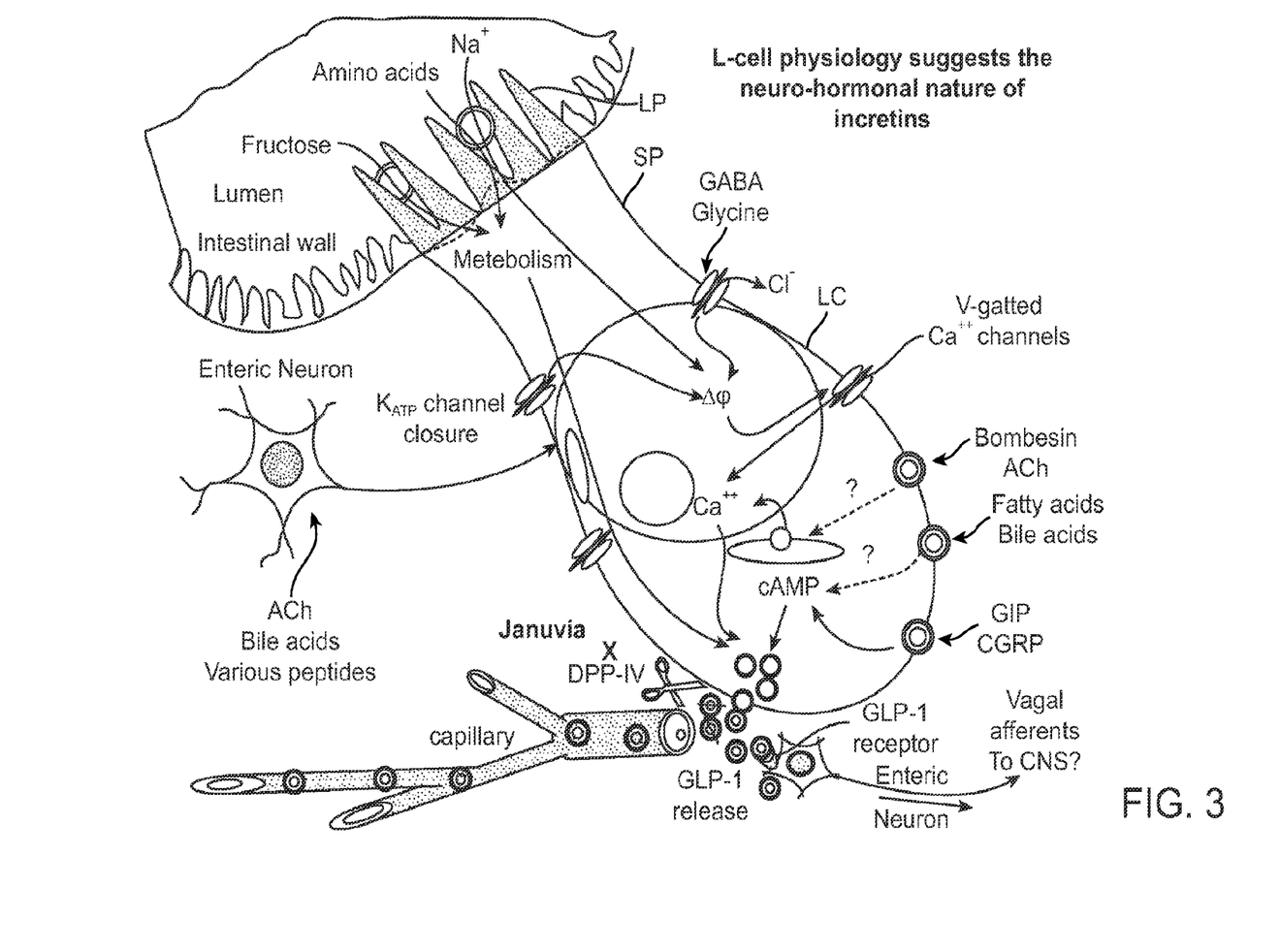
FIG. 3 is a schematic view illustrating the biochemical and physiological function of the L-cell including hormonal secretion and intracellular signaling.

Referring now to FIGS. 1-3, the mucosal surface of the intestinal tract including the small and large intestine are lined with a number of cells, including L-Cells (LC) and K-cells (KC). The L-cells include a sub-mucosal portion SP and a luminal projecting portion LP which extends from the surface of the mucosa M and binds with various molecules including glucose. L-cells and K-cells secrete various gastrointestinal hormones known as incretins including glucagon like protein (GLP-1), glucose-dependent insulinotropic peptide GIP and oxyntomodulin (OXM).

The hormone GIP can enhance secretion of GLP-1. GIP is secreted by so-called "K" cells in the proximal duodenum, under some degree of control by enteric cholinergic neurons. The L-cells as well as K-cells secrete GLP-1 and GIP in response to exposure to glucose. In turn, GIP acts to increase release of GLP-1. GLP-1 in turn, acts to increase the production of insulin as is discussed below. Incretins produce other beneficial effects such as appetite suppression, weight loss, restoration of insulin-sensitivity of body tissue and preservation of beta-cells of the pancreas. Incretins are rapidly metabolized/degraded by the kidney and peptidases (half-life GLP-1<2 mins., GIP<7 mins.).

Incretins are thought to play an important role in glucose control within the body in that incretins such as GLP-1, increase insulin secretion in a glucose dependent manner in a phenomenon known as the "incretin effect." In fact, approximately 50% or more of the insulin response to a meal is attributed to the incretin effect. The incretin effect causes a fairly rapid increase in plasma insulin, usually within about the first 30 minutes after ingestion of glucose. Many patients with type 2 diabetes have a significant reduction of the incretin effect including a reduction in GLP-1 secretion and a substantial reduction in the insulinotropic activity of GIP. This results in a substantial reduction in the rate and amount of insulin production in diabetic patients.

Several approaches can be contemplated for reversing the loss of the incretin effect occurring in diabetes including Type II diabetes. These include increasing the production of GIP and/or GLP-1. As discussed above, in patients with Type II diabetes, GIP loses its insulinotropic activity and is thus no longer able to modulate glucose-dependent insulin secretion, even at supraphysiological (pharmacological) plasma levels. The loss of this activity is detrimental to the production of insulin by the .beta.-cells of the pancreas, especially after eating. Therefore, increasing GIP production may not be a viable option. However, GLP-1 is still insulinotropic in Type II diabetes, albeit with significantly reduced levels. Therefore, increasing levels of GLP-1 appears to be an approach for increasing insulin production in diabetic patients including patients with Type II diabetes.

Accordingly, various embodiments of the invention contemplate increasing the production of GLP-1 and other incretins by electrically stimulating portions of the intestines concurrently or substantially concurrently to the ingestion of a meal. This can be achieved by ingesting a swallowable capsule before, during or after the ingestion of a meal, wherein the capsule is configured to electrically stimulate portions of the intestine to stimulate L-cells to secrete GLP-1 and other incretins to increase insulin production. Desirably, the capsule is swallowed in a coordinated fashion with the ingestion of a meal (e.g., during a selected time before, during or after the ingestion of a meal, e.g., 1-30 minutes before or after the ingestion of a meal) such that secretion of GLP-1 or other incretin is coordinated with the absorption of nutrients into the blood stream. The coordination or timing of the capsule with the ingestion of a meal can also be selected to produce other effects such as appetite suppression described herein.

Referring now to FIGS. 4-8, an embodiment of a swallowable capsule 10 for stimulating L-cells and other cells in the intestinal tract IT to secrete incretins includes a capsule body 20, at least two or more electrodes 40 for providing electrical stimulation to desired cells, a controller 30 for controlling one or more operations of the capsule and generating the electrical signals delivered to the tissue by the electrodes, a power source 55 for powering one or more components of the capsule such as the controller and at least one sensor 60 for determining the location of the capsule in the tract and/or various events and conditions in the GI tract. In various embodiments discussed herein, capsule 10 may also include an accelerometer 65 for measuring the rate of travel of the capsule through the intestinal tract IT and determining periods of no movement.

Figure 4:
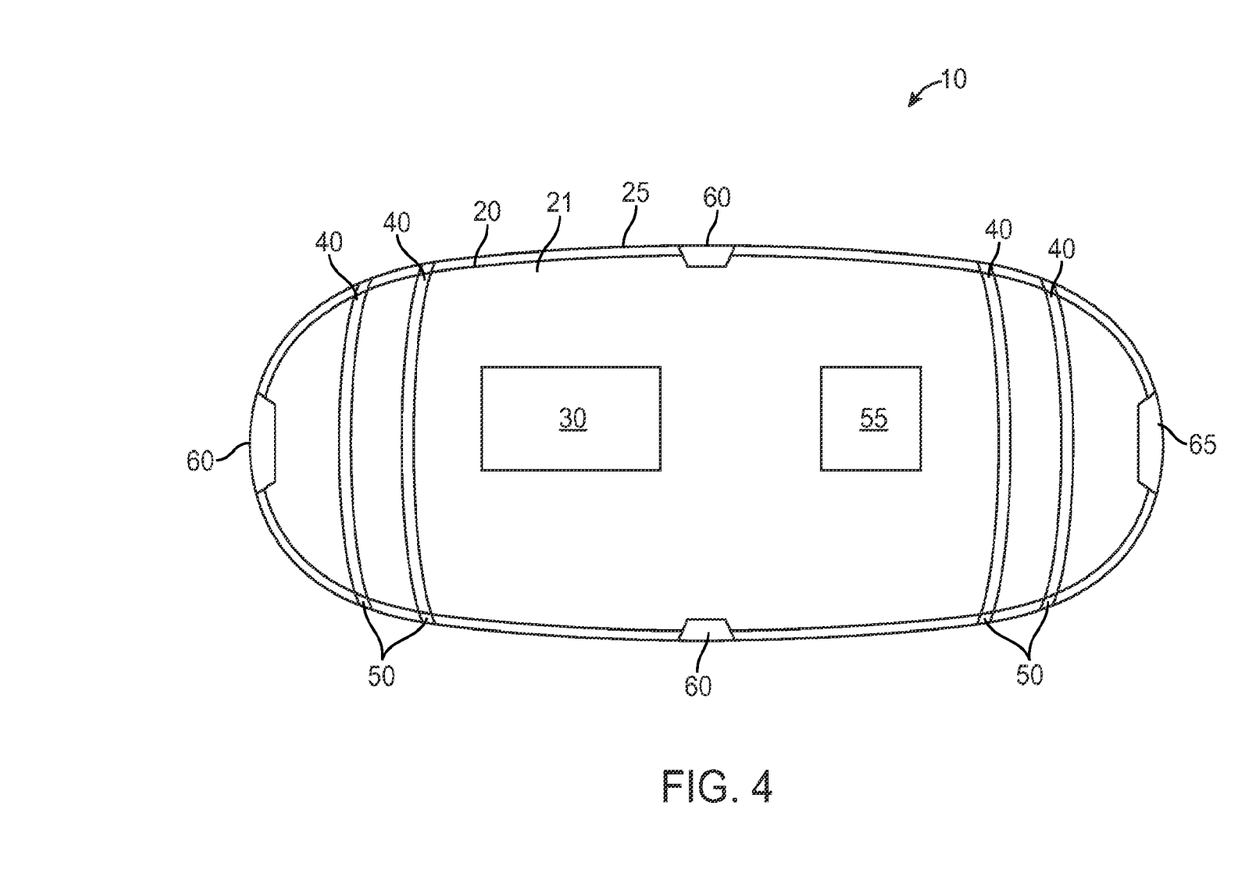
FIG. 4 is a lateral view showing an embodiment of the swallowable capsule of the present invention.

Capsule body 20 (herein referred to as body 20) is desirably sized and shaped to be swallowed by the user (also referred to herein as the patient) and pass completely through the intestinal tract with normal peristaltic movement. Body 20 includes a body surface 25 and interior cavity 21 for various components, e.g., controller 30, etc. Body 20 can be fabricated from various biocompatible inert plastics known in the art and can also include various coatings (e.g., enteric coatings).

Electrodes 40 can comprise various biocompatible conductive materials including silver-silverchloride, platinum or stainless steel. Still other conductive materials known in the art, such as various conductive polymers are also contemplated. Electrodes 40 can also have a laminated construction with a more corrosion resistant material on the surface. Typically, electrodes 40 will include at least one electrode pair 50 of electrodes which can be configured as bipolar electrodes. Multiple pairs 50 of electrodes 40 are contemplated including two, three, four and still larger numbers.

Figure 7A:
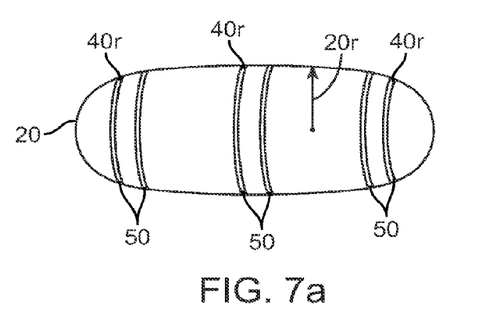
FIG. 7a is a lateral view showing an embodiment of the capsule having ring electrodes.

Electrodes 40 can be positioned in a variety of manners on the surface 25 of the capsule body 20. This includes in a lengthwise fashion with respect to radius 20r of the capsule, as is shown in embodiment of FIG. 7a. FIG. 7a also shows an embodiment where electrodes 40 comprise one or more pairs 50 of ring electrodes 40r which are placed on the surface capsule. Multiple pairs 50 of ring electrode 40r can be distributed along the length of the capsule 20 with each pair being switchable by controller 30 or other switching circuitry. Such embodiments allow controller 30 to switch individual electrode pairs 50 on and off so as to optimize the stimulation of L-cells based on a variety of factors, for example, when a peristaltic contraction or squeeze is detected on one portion of the capsule, but not another.

Figure 7B:
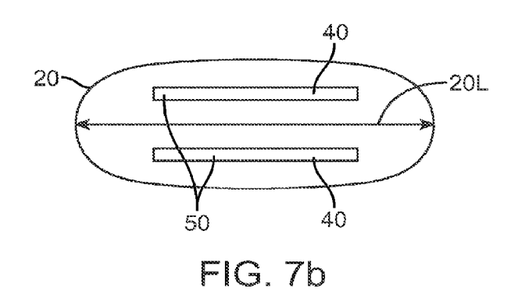
FIG. 7b is a lateral view showing an embodiment having laterally oriented electrodes.
Figure 7C:
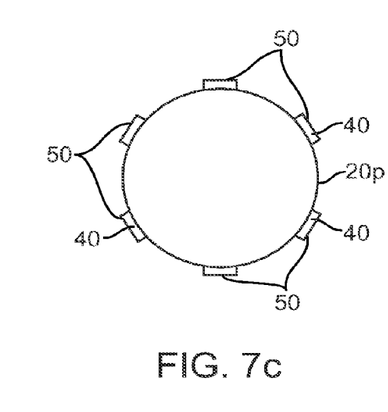
FIG. 7c, is a cross sectional view showing an embodiment having multiple laterally oriented electrodes.
Figure 7D:
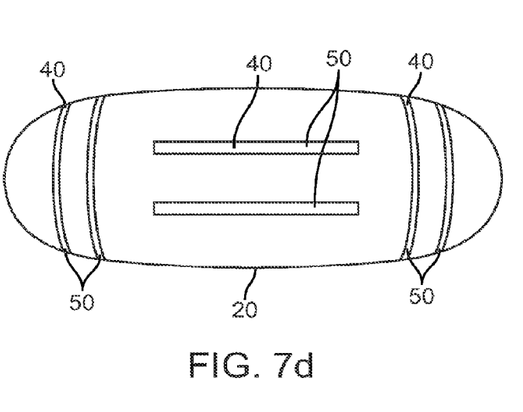
FIG. 7d is a lateral view showing an embodiment having both ring and laterally oriented electrodes.

In other embodiments, electrodes 40 can be oriented in a lengthwise fashion with respect to the longitudinal axis 20L of the capsule 20 as is shown in the embodiment of FIG. 7b. In preferred embodiments, capsule 20 can include multiple pairs 50 of electrodes 40 oriented with respect to lateral axis 20L so that they are distributed around the capsule perimeter 20p as is shown in the embodiment of FIG. 7c. In still other embodiments, capsule 20 can include a combination of laterally and radially oriented electrodes as is shown in the embodiment of FIG. 7d. Such embodiments can be used for stimulating different types of cells (e.g., L-cells and K-cells), cells in different locations, or as is discussed herein, for stimulating L-cells and also stimulating intestinal muscle tissue to evoke a peristaltic contraction.

Figure 6:
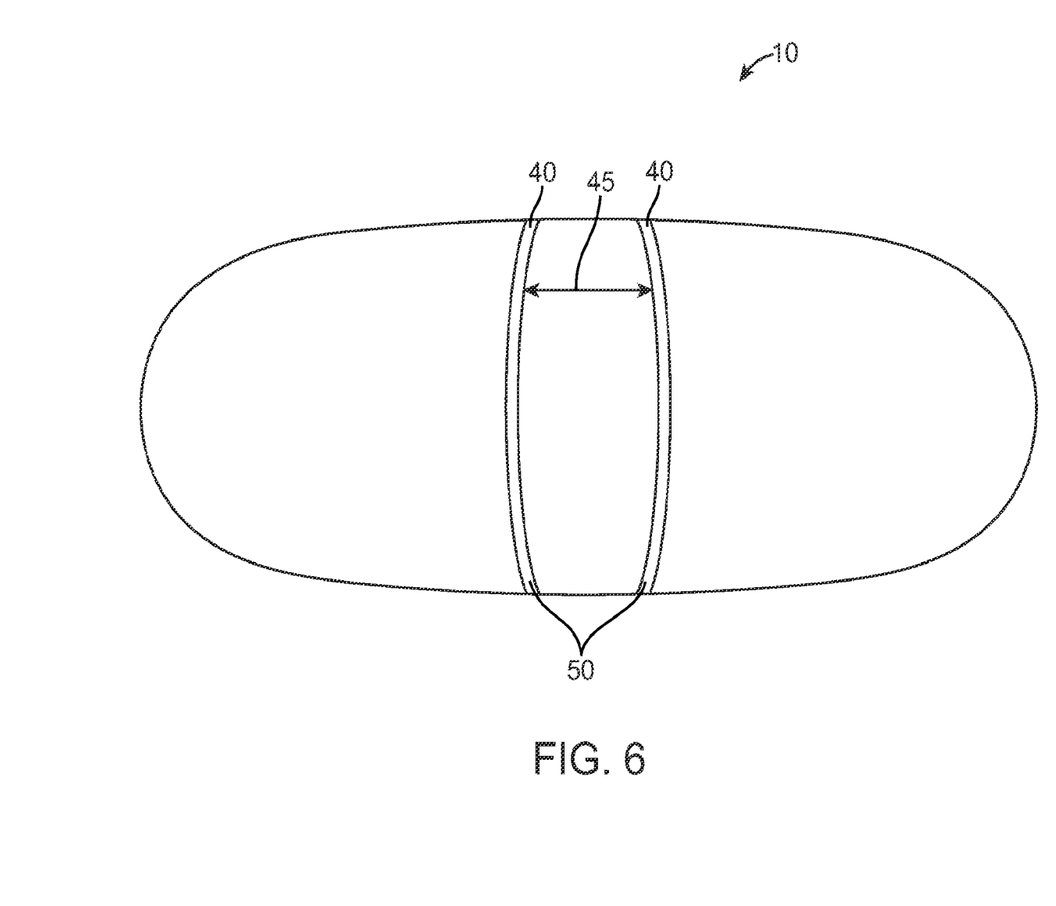
FIG. 6 is a lateral view showing the gap between the electrodes of an embodiment of the swallowable capsule.

Desirably, the spacing or gap 45 between individual electrodes is configured to minimize electrical stimulation of tissue subjacent the mucosal layer of intestinal tract as is shown in the embodiment of FIG. 6. The spacing 45 can be configured to limit the electrical stimulation of the intestinal wall to a depth of 5 mm or less more preferably 3 mm or less and still more preferably 1 mm or less. In particular embodiments, gap 45 can be in the range from about 0.05 to about 0.2 inches with specific embodiments of 0.1, 0.15 inches. Closer spacing can be used to achieve a shallower stimulatory effect. Particular embodiment can have varied spacing between electrodes pairs 50 with some pairs configured for a shallower stimulatory effect and others configured for a deeper stimulatory effect. In the latter case, the deeper stimulatory effect can be configured for stimulating the intestinal muscle tissue to evoke a peristaltic contraction of the intestine as is discussed herein.

Power source 55 will typically comprise a miniature chemical battery such as a lithium or lithium-ion battery. For battery embodiments of power source 55, the battery can be configured to provide at least 5 or more hours of battery life. Controller 30 can include various power management circuitry to optimize battery life. In various alternative embodiments power source 55 can also comprise a piezo-electric power source that uses piezo electric materials configured to harvest energy from compression or deformation of the capsule by movement of the capsule through the intestinal tract. In still other embodiments, the power source can comprise a thermo-electric power source such as a peltier effect power source device configured to use heat from the patient's body to generate power. In such embodiments, all or a portion of the capsule can include a thermally conductive layer or other thermal conductive element configured to conduct heat to the peltier effect device.

In various embodiments, the at least one sensor 60 can include one or more of a pH sensor and a pressure/force sensor. The pH sensor can be configured for detecting passage of the capsule from the stomach into the small intestine, as indicated by a rapid rise in pH when the capsule passes through the pyloric valve and into the duodenum. Various miniature pH sensors known in the art can be utilized. The pressure sensor 60 can be utilized for sensing the peristaltic contraction of the intestines so as to detect when the capsule is in the intestine. The pressure sensor 60 can be used to detect when intestine is in contact with capsule (e.g., when it's being squeezed during a peristaltic contraction or peristaltic squeeze) and thus when to initiate a period of stimulation. Various miniature solid state pressure/force sensors can be used such as various miniature strain gauge sensors including various micro-electrical-mechanical systems (MEMS) based strain gauges or other related pressure/force sensor. Particular embodiments can include both pH and pressure sensors so as to determine a change in pH from the stomach to the intestine and peristaltic contraction providing increased level of accuracy in determining the position of the sensor within the tract. In various embodiment, multiple pH and pressure sensors 60 can be distributed over capsule body surface 25 so as to determine when one portion of the capsule has entered the intestine, or determine when one portion is being squeezed by peristaltic contraction (and thus electrodes in that section can be switched on) or other pressure differential inactive of a change in location or state of the capsule.

Still other sensors are contemplated, such as temperature, $O_2$, $CO_2$, optical, acoustical sensors, etc. Further, the inputs from multiple sensors may be combined to generate an aggregate sensory input for the controller to determine the position of the capsule. Also as is discussed herein, in various embodiments, sensor conditioning circuitry 63 can be coupled to controller 30 to condition the sensor signals 61 prior to being inputted to controller 30.

Figure 5:
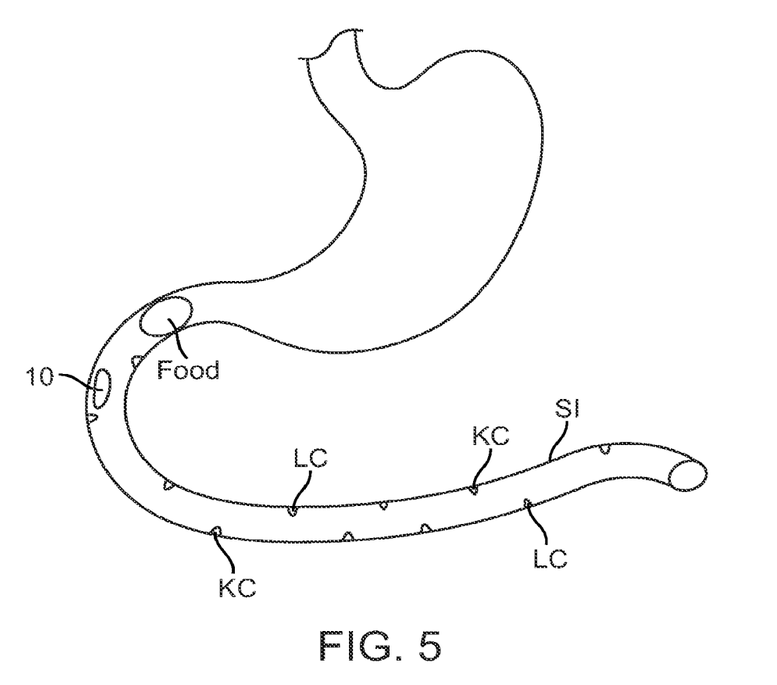
FIG. 5 is a cross sectional view illustrating use of an embodiment of the swallowable capsule in the intestinal tract to stimulate L-cells to secrete incretins.

Referring now to FIG. 5, in one embodiment of a method of use, the swallowable capsule 10 of the present invention can be used to facilitate insulin release and/or enhance its activity in the body. Upon ingestion, the swallowable capsule 10 makes its way through the stomach into the small intestine SI. Sensors 60 in the capsule 10 allow its relative position in the body to be detected. For example, sensors for pH, pressure, or other pertinent indicia allow the capsule to determine when it has gone past the pyloric sphincter and reached the small intestine. In the case of pH measurements, this can be determined by a sharp rise in pH occurring after the capsule has gone past the pyloric sphincter and into the duodenum.

Once in the small intestine, swallowable capsule 10 is activated to provide electrical stimulation so that L-cells of the small intestine secrete GLP-1 or other incretins (GIP, PYY, etc.). The GLP-1 and/or other incretins then elicit secretion of insulin and/or facilitate the body's use of insulin. Activation of the swallowable capsule to provide electrical stimulation may, for example, be directed by internal instructions and/or programs within the controller or other logic resources disposed in the swallowable capsule, or may be provided by external control of the swallowable capsule.

Because in some patients, the L-cells tend to be more concentrated distally, (particularly in diabetic patients who have an uneven distribution with the majority located distally) the capsule controller 30 may, in particular embodiments, initiate a timer upon reaching the small intestine so that the controller may estimate how far the capsule has traveled in the small intestine. This distance can be estimated with the use of average transit times through the gut or an individual measurement of transit time for the particular patient using known methods in the GI diagnostic arts. Appropriate delays in the initiation of stimulation can then be determined using the timer function. Longer delays can be used for patients having longer transit times. In embodiments having an accelerometer, the actual speed of the capsule through the intestine can be calculated and utilized to determine when to initiate a stimulation signal after the capsule has entered into the small intestine. Also as discussed below, adjustments in the timing of the L-cell stimulating signal can be made for embodiments using a peristaltic contraction stimulating signal.

As an alternative or adjunct to the use of a pH sensor for determining capsule position including when the capsule has entered the small intestine, capsule 10 can also include a pressure sensor 60 to detect when the intestinal walls are squeezing the capsule e.g., from a peristaltic contraction. Appropriate pressure/force levels indicative of intestinal squeezing can be determined from known physiological measurements or can established by looking for a relative increase in squeezing pressure (e.g. 2×, 3×, 5× or an order of magnitude or more). In some embodiments, the detection of squeezing by the intestinal wall can also serve as a trigger to initiate electrical stimulation of the L-cells as it may be desirable to have the electrodes in contact with or otherwise close to the intestinal walls. Such contact or proximity may serve to more effectively deliver current to, and depolarize, the L-cells to produce GLP-1. Also, in related embodiments, once a decrease in pressure is detected (indicating a relaxation of the intestinal wall away from the capsule), electrical stimulation can be stopped (either initially or after a programmed delay) so as to conserve battery power during a time when stimulation may produce a sub-optimal release of GLP-1 or other incretin. Thus in this way, the stimulating signals from the electrodes can be turned on and off with each peristaltic contraction of the intestine (either the small or large intestine) until the capsule has transited all or a selected portion of the intestine.

Preferably, the swallowable capsule is ingested with a meal so that the stimulation of the L-cells (or other cells) to secrete GLP-1 and/or other incretins is coordinated with absorption of nutrients from the meal so that subsequent insulin production is also coordinated with the influx of glucose, fats and other nutrients into the blood stream. In this way, insulin is delivered in a manner to mimic normal physiologic delivery of insulin upon digestion of food and thus achieve improved blood glucose management. This process can be refined even further by using standard glucose monitoring methods (e.g., a blood glucose meter) to monitor blood glucose levels following a meal and then make adjustments in the delay or other timing of the stimulation signal. In some embodiments, the capsule can be configured to allow the user to input to the capsule, the amount and type of food being consumed (e.g., a high carbohydrate or high fat meal, which is more likely to produce a spike in blood glucose). A software module resident within or coupled to controller 30 or other logic resources within capsule 10 can then adjust the timing and sequence of the L-cell stimulating signal so as to titrate the levels of generated insulin in response to food consumed. The inputs to the capsule can be signaled by a handheld device such as a cellular phone or like device using BLUETOOTH or other wireless connectivities or protocols known in the art. In these and related embodiments, capsule 10 can include an RF-communication chip.

Figure 8:
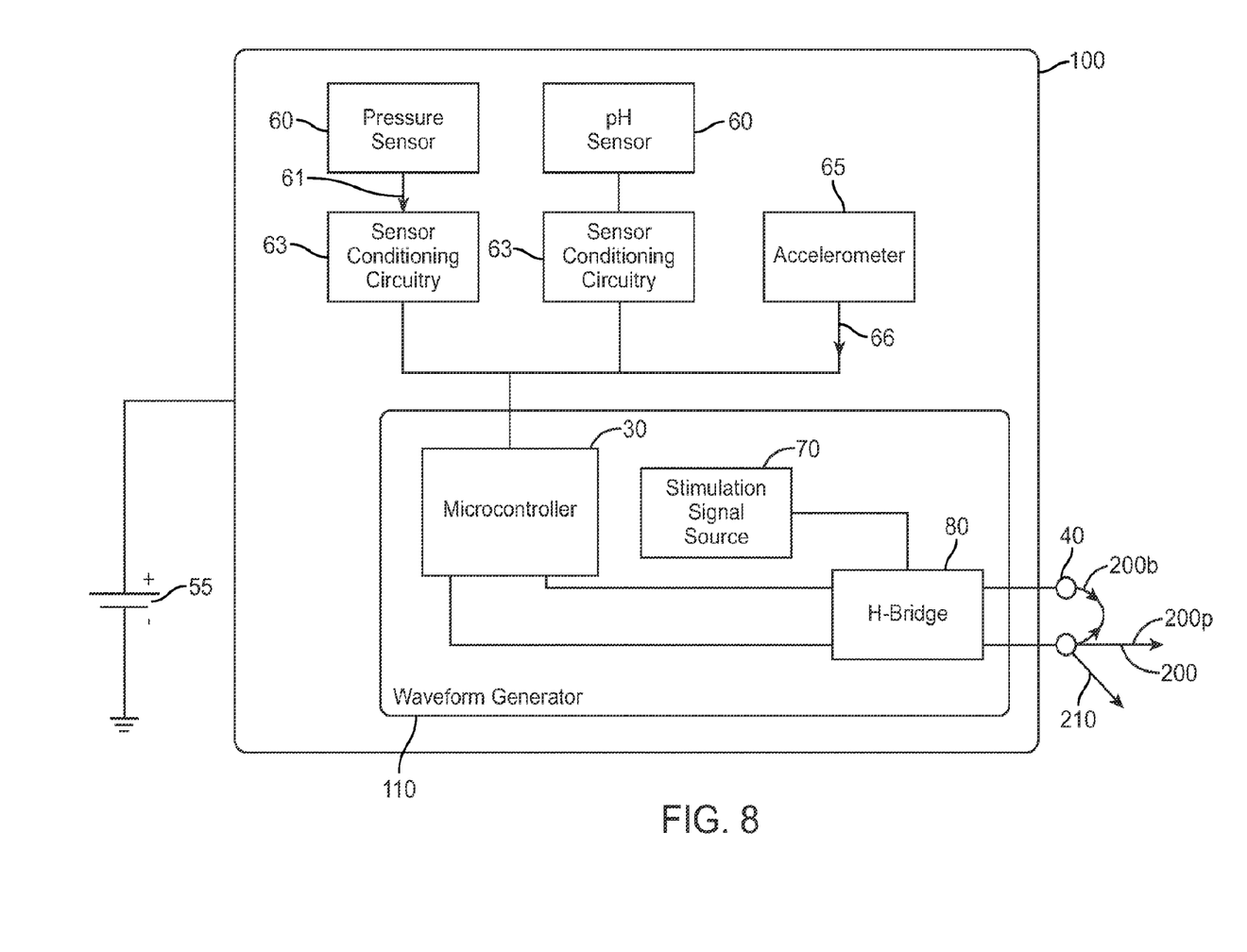
FIG. 8 is a block diagram showing an embodiment of an electronic architecture for controlling one or more functions of the swallowable capsule.
Figure 9A:
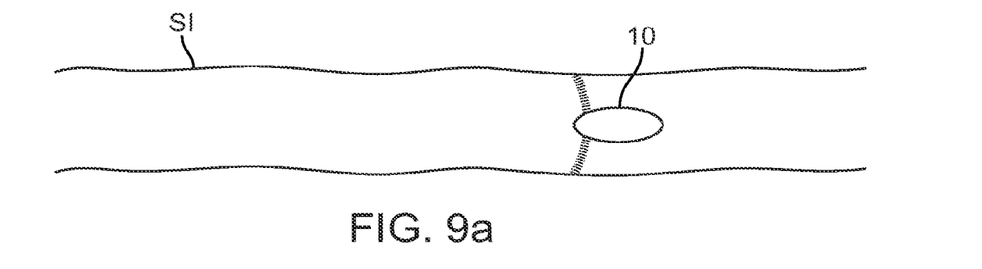
FIGS. 9a-9d are lateral views illustrating use of an electrically stimulating waveform emitted from the capsule to evoke peristaltic waves to move the capsule through the intestinal tract.
Figure 9B:
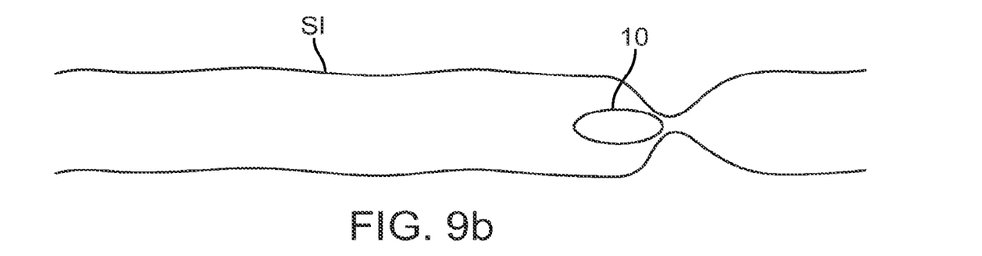
Figure 9C:
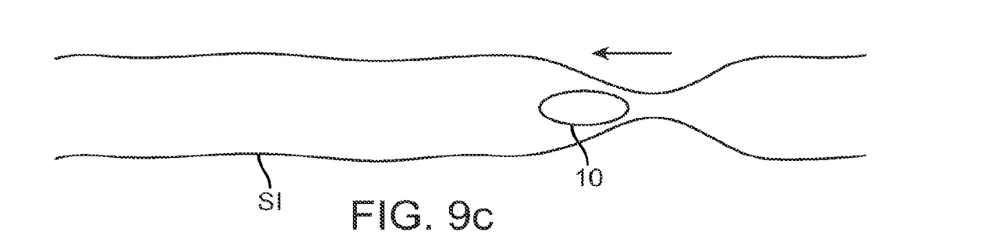
Figure 9D:
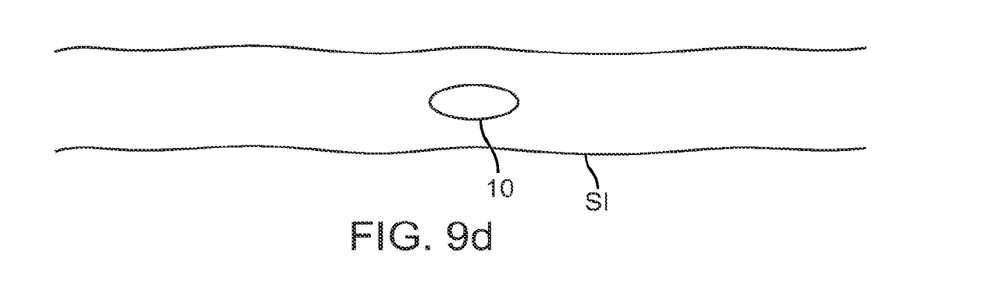

Referring now to FIG. 8, embodiments of a circuit architecture 100, for controlling one or more functions of capsule 10 will now be discussed. Architecture 100 will typically comprise a controller 30, sensors 60 (such as pressure and pH sensor), sensor conditioning circuitry 63, a stimulation signal source 70 (herein signal source 70), an H-bridge or like device 80. Controller 30 will typically comprise a microcontroller such as a microprocessors or state device and can be coupled to one or more other electronic components of capsule 10 as is shown in the embodiment of FIG. 8. Also as shown in the figure, power source 55 can be coupled to one or more components of architecture 100, (e.g., controller 30, sensor 60, stimulation signal source 70, etc.) so as to provide power to those components. Sensor conditioning circuitry 63 can include standard circuitry known in the art and serves to condition (e.g., filter via high pass or low pass filter) inputs 61 received from sensors 60. Signal source signal 70 comprises a variety of energy conversion circuits that translates a fixed DC voltage from a battery or other power source 55 into a programmable energy modality. Suitable energy conversion circuits for signal source 70 can include one or more of the following: a programmable current source, programmable voltage source, a DC-DC converter or a DC-AC converter. H-bridge device 80 supplies signals to electrodes 40 and can be configured to change the direction of current flow between electrodes 40 so as to produce a biphasic stimulation signal (described below) as well as stop the flow of current altogether (via means of one or more switches actuable by controller 30).

Collectively, controller 30, stimulation signal source 70 and H-bridge 80 comprise a signal generator 110, also known as waveform generator 110 which generates stimulation signals 200 that are delivered to electrodes 40 and then conducted to intestinal tissue (e.g., the intestinal wall) for stimulating L-cells (or other cells) for producing incretins such as GLP to stimulate insulin production or enhance the effect of insulin. Desirably, signal 200 is configured such that it will stimulate the L-cells to produce incretins such as GLP-1 but will not cause peristaltic contractions of the intestinal site near the capsule 200 or any other location in the intestinal tract. This quality can be achieved by control of one or more of the current, voltage and/or frequency of the signal as well as pulse duration for pulsed signals as described herein. For L-cell (and K-cell) stimulating purposes, signals 200 can have voltages ranging from about 0.1-10V, currents ranging from about 10 μa to 2 mA and frequencies ranging from 1 Hz-100 Hz. Voltage, current and frequency can also be fine tuned or otherwise adjusted for the condition to be treated (e.g., diabetes, obesity, etc.), the severity of the condition (e.g., type I vs. type II diabetes) and other patient conditions (such as intestinal neuropathy).

Signals 200 can have a variety of waveforms such as square wave, sine wave, saw tooth, trapezoidal, for example. In preferred embodiments, signal 200 can comprise a biphasic signal 200b, which can be generated using an H-bridge device 80 as is described above. In many embodiments, including those having a square waveform signal 200 can comprise a pulsed signal 200p. Pulsed signals 200p can have pulse widths ranging in the range of 10 μs-100 ms.

As described above, the signal 200 is desirably configured such that it will stimulate L-cells (or other related cells such as K-cells) to produce incretins such as GLP-1 but will not cause peristaltic contractions of the intestinal site near the capsule or any other location in the intestinal tract. However in some embodiments, waveform generator 110 can also be configured to produce two waveforms, a first waveform 200 for stimulating the L-cells without causing peristaltic contractions and a second waveform 210 for causing peristaltic contractions so as to advance capsule 10 along the intestinal tract. In these later embodiments, the capsule can include an accelerometer 65 for detecting when the capsule 10 has stopped moving or is moving below a desired velocity threshold. In use, these latter embodiments allow for capsule 10 to be advanced in patients who have a very slow moving intestinal tract such as those patients who have intestinal neuropathy or other related condition such as intestinal necrosis. When controller 30 receives an input 66 from the accelerometer 65 indicating that capsule 10 has stopped or is moving too slow the controller can produce a signal for the waveform generator 110 to generate the second waveform 210 causing peristaltic contraction of the intestine in the region near the capsule which, in turn, propels the capsule distally through the intestine. The process can be repeated as needed with selectable delays to allow for the refractory period of the peristaltic contraction.

Referring now to FIGS. 9a-9d, a discussion will now be presented of an embodiment of a method for propelling the capsule through the intestine by evoking peristaltic contractions. As discussed herein, some patients, particularly diabetic patients, have a condition known as intestinal neuropathy wherein the transit time of food through the small and/or large intestine is greatly reduced due to damage of the motor neurons innervating the intestine. Accordingly, in particular embodiments, the controller can also be configured to produce two stimulating signals, one signal having a first waveform for stimulating the L-cells without causing peristaltic contractions and a second signal having a second waveform for evoking peristaltic contractions so as to advance the capsule along the intestinal tract. As discussed herein, the second signal can have higher stimulation currents than the first signal, for example, in the range of 2-5 ma. In embodiments using a peristaltic stimulating signal, capsule 10 can include an accelerometer 65 for detecting when the capsule has stopped moving or is moving below a desired velocity threshold. When controller 30 detects that the capsule is below a desired threshold or that that the capsule has been stationary beyond a desired time period (e.g., 0.5 to 2 minutes with longer and shorter periods contemplated), it initiates the generation of one or more peristaltic stimulating signals to cause a peristaltic contraction to propel the capsule distally through the intestine. An appropriate delay can then be built in before an L-cell stimulating signal is delivered to allow for the peristaltic contraction to occur as well for the electrical refractory period of the intestine. If desired, multiple peristaltic evoking signals can be generated to cause a series of peristaltic contractions, for example, for patients who have particular slow transit time or when the capsule is just entering the small intestine so as to move the capsule more distally within the intestinal tract before L-cell stimulating signals are delivered. In use, such embodiments allow for the capsule to be advanced in patients who have a very slow moving intestinal tract such as those patients who have intestinal neuropathy or other related condition such as intestinal necrosis. When the controller receives an input from the accelerometer indicating that the capsule has stopped or is moving too slow, the controller generates the second waveform causing peristaltic contraction of the intestine in the region near the capsule which in turn propels the capsule distally through the intestine. The process can be repeated as needed with selectable delays to allow for the refractory period of the peristaltic contraction.

EXAMPLES

Various embodiments of the invention will now be further illustrated with reference to the following examples. However, it will be appreciated that these examples are presented for purposes of illustration and the invention is not to be limited by these specific examples or the details therein.

Example 1

Electrical Stimulation of In Vitro GLP-1 Release

Culture dishes were coated on ice with Matrigel by adding 50 ul/cm$^2$ (190 ul in 24 well dishes). The dishes were warmed at 37° C. for 30 minutes, and then seeded with 260,000 cells using high glucose DMEM supplemented with 2 mM glutamine (0.146 g per 500 ml), 10% fetal bovine serum (FBS), and 1% Pen Strep. After 48 hours there were 1.5-2 million cells per well. The initial cells were NCI-H716 cells, which are a human poorly differentiated colorectal adenocarcinoma. These cells grew undifferentiated in suspension. However, after the 48 hour treatment described above, the cells differentiated into GLP-1 secreting cells. These GLP-1-secreting cells were used for the following experiment.

For the experiment, the cell medium was replaced with HBSS supplemented with 0.5% FBS and optionally one of the following test agents:

1. PMA (phorbol-12-myristate-13-acetate) (stock solution of 1 mg in 1.6 ml DMSO=1 mM; add 1 ul per ml of media, giving a final concentration of 1 uM)
2. 1.5% sucrose
3. 10% glucose
4. Electrical stimulation (250 uA, 5 Hz, alternating pulse wave of 0.1, 1.0 or 10 msec)

The cells were cultured for 2 hours. Test agents were added and cell supernatants were removed at various time points for analysis. PMSF (10 ul) was added to the cell supernatants, which can be frozen or used immediately. A lysis buffer was prepared by combining RIPA with 10 ul PMSF, 10 ul proteinase inhibitor, and 10 ul sodium orthovate. 200-300 ul of the RIPA lysis buffer was then added to a well along with the cell supernatant sample. The well was scraped with a cell scraper and the mixture was pipetted into a 1.5 ml tube, followed with repipetting to break up cells and cell membranes. The tubes were spun down at full speed for 5 min, the supernatants were collected and then frozen or immediately analyzed.

Figure 10:
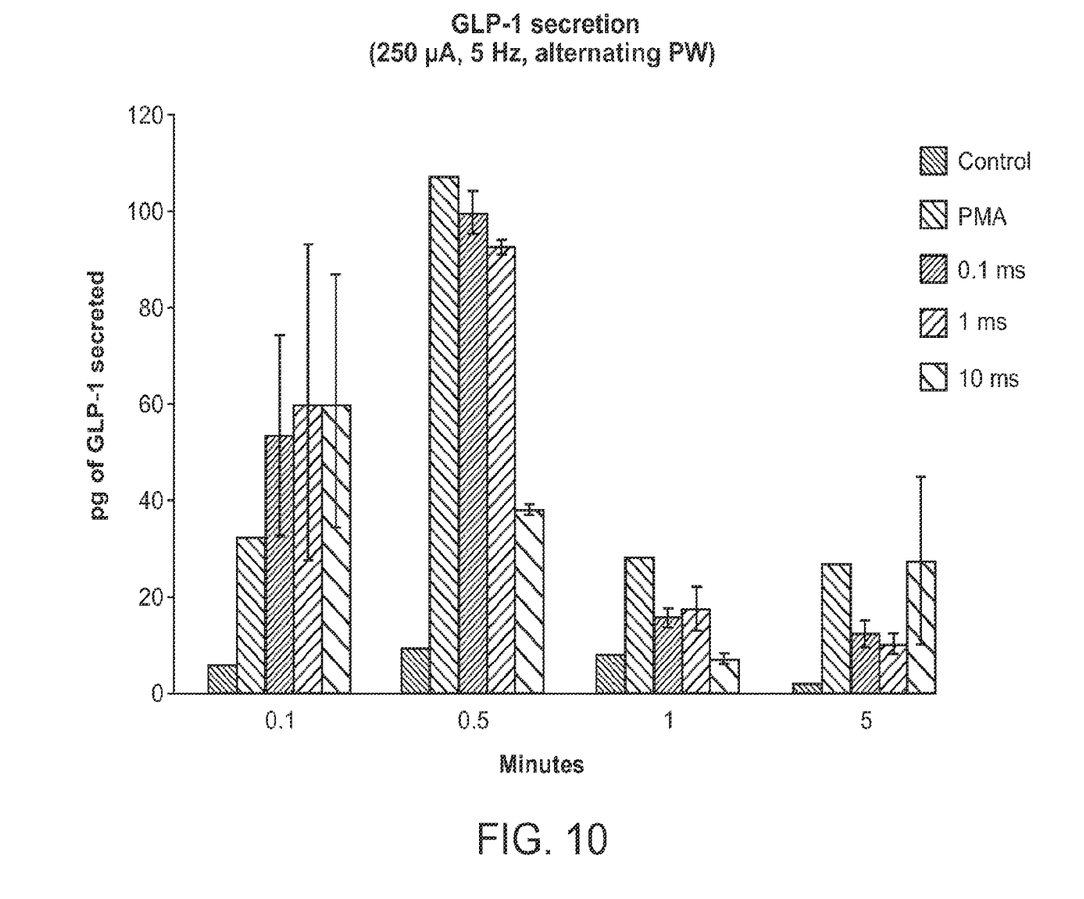
FIG. 10 is a bar graph showing the effect of electrical stimulation on in vitro production of GLP-1 by differentiated NCI-H716 cells.
Figure 11:
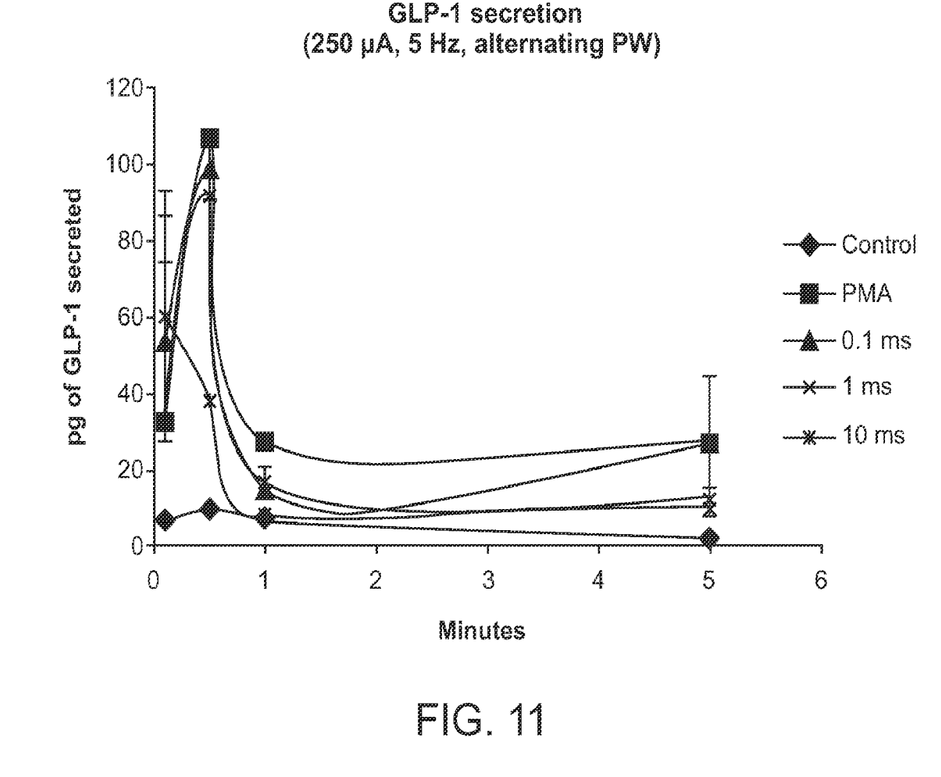
FIG. 11 is a time course graph showing the effect of electrical stimulation on in vitro production of GLP-1 by differentiated NCI-H716 cells.

GLP-1 was determined by ELISA. Streptavidin coated wells were incubated with a biotin-conjugated antibody which specifically binds GLP-1. After incubation with the lysed cell supernatants, the samples were then incubated with GLP-1-binding antibody conjugated to HRP (horseradish peroxidase). Substrate conversion by HRP was then used to quantitate GLP-1. The results are shown in FIGS. 10 and 11.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the capsule can be sized for various pediatric applications. Also the waveform can be configured to inhibit as well as stimulate various cells in the intestinal tract. For example, the waveform can be configured to stimulate one cell type and inhibit another. Additionally, various embodiments of the capsule can include telemetry for signaling to and from an external monitoring and/or control device.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for stimulating hormone producing cells (HP-cells) in the intestinal tract of a patient to secrete a glucose regulating hormone (GR-hormone), the method comprising:
    ingesting a swallowable device configured to travel through the intestinal tract and electrically stimulate the HP-cells at any location in the intestinal tract;
    delivering an electrical signal from the device to an intestinal wall proximate the device, wherein the signal includes a waveform configured to electrically stimulate HP-cells in the intestinal tract to secrete the GR-hormone with normal peristaltic contraction of the intestinal tract.

2. The method of claim 1, wherein the intestinal wall is a wall of the small intestine.

3. The method of claim 1, wherein the HP-cells comprise K-cells or L-cells.

4. The method of claim 1, wherein the secreted GR-hormone comprises an incretin or GLP-1.

5. The method of claim 1, further comprising:
    modulating a release of insulin in the patient responsive to the secreted GR-hormone.

6. The method of claim 5, wherein the insulin release is modulated by the electrical stimulation of the HP-cells to produce an increase in plasma insulin within 30 minutes of stimulation.

7. The method of claim 1, further comprising:
    controlling a blood glucose level of the patient responsive to the secreted GR-hormone.

8. The method of claim 1, further comprising:
    suppressing an appetite level of the patient responsive to the secreted GR-hormone.

9. The method of claim 1, wherein the waveform has a square wave shape.

10. The method of claim 1, wherein the waveform includes a first wave form and a second waveform, the first wave form configured to stimulate the HP-cells without causing a peristaltic contraction.

11. The method of claim 10, wherein the second waveform is configured to generate a peristaltic contraction of intestinal tissue proximate the device, the method further comprising:
    advancing the device within the intestinal tract using the generated peristaltic contraction.

12. The method of claim 10, wherein the second waveform occurs substantially non-concurrently with the first waveform.

13. The method of claim 10, wherein the second waveform is generated responsive to a velocity of the device moving through the intestinal tract.

14. The method of claim 13, wherein the velocity is measured using an accelerometer disposed on or within the device.

15. The method of claim 1, further comprising:
    determining a location of the device in a GI tract, wherein the signal is delivered responsive to the location of the device in the intestinal tract.

16. The method of claim 15, wherein the location is a small intestine.

17. The method of claim 15, wherein the location is determined using a sensor.

18. The method of claim 17, wherein the location is determined based on at least one of a sensed pH or sensed pressure applied to the device surface by intestinal wall tissue.

19. The method of claim 1, wherein the ingestion of the device is coordinated with a ingestion of food.

20. The method of claim 19, wherein the device is ingested during a selected time period before, during or after the ingestion of food.

21. The method of claim 19, wherein a time period is selected to coordinate the stimulation of the HP-cells with the absorption of nutrients from the food into a blood stream.

22. The method of claim 1, wherein the device comprises a swallowable capsule.

23. The method of claim 1, wherein the device comprises a controller, at least one electrode and a waveform generator.

24. A method for stimulating hormone producing cells (HP-cells) in the intestinal tract of a patient to secrete a hormone which modulates a release of insulin, the method comprising:
    ingesting a swallowable device configured to travel through the intestinal tract and electrically stimulate the HP-cells at any location in the intestinal tract;
    delivering an electrical signal from the device to a intestinal wall proximate the device, wherein the signal includes a waveform configured to electrically stimulate the HP-cells in the intestinal tract to secrete the hormone with normal peristaltic contraction of the small intestine; and
    modulating the release of insulin in the patient responsive to the secreted hormone.

25. The method of claim 24, wherein the insulin release is modulated by the electrical stimulation of the IP-cells to produce an increase in plasma insulin within 30 minutes of stimulation.

26. The method of claim 24, wherein the hormone comprises an incretin or GLP-1.

27. The method of claim 24, further comprising:
    increasing the insulin sensitivity of the patient's body tissue responsive to the secreted hormone.

28. The method of claim 24, further comprising:
    controlling a blood glucose level of the patient responsive to the secreted hormone.

29. The method of claim 24, wherein the HP-cells comprise K-cells or L-cells.

* * * * *